United States Patent [19]
Scheinberg

[11] Patent Number: 5,899,207
[45] Date of Patent: May 4, 1999

[54] PROTECTING SKIN FROM FRICTION

[75] Inventor: Samuel Scheinberg, Neotsu, Oreg.

[73] Assignee: The Seaberg Company, Inc., South Beach, Oreg.

[21] Appl. No.: 09/039,742

[22] Filed: Mar. 16, 1998

[51] Int. Cl.⁶ ..................... A61F 5/37
[52] U.S. Cl. ............ 128/882; 128/893; 128/894
[58] Field of Search .................. 128/845, 846, 128/869, 882, 893, 894; 602/41, 47, 54

[56] References Cited

U.S. PATENT DOCUMENTS

| | | | |
|---|---|---|---|
| 1,913,928 | 6/1933 | Kaufman . | |
| 2,098,312 | 11/1937 | Scholl | 128/153 |
| 2,261,041 | 10/1941 | Tennant | 128/894 |
| 2,712,311 | 7/1955 | Scholl | 128/894 |
| 2,918,062 | 12/1959 | Scholl | 128/894 |
| 3,062,208 | 11/1962 | Scholl | 128/894 |
| 3,260,261 | 7/1966 | Gallovich | 128/149 |
| 3,548,420 | 12/1970 | Spence | 3/20 |
| 3,821,954 | 7/1974 | Grubel | 128/149 |
| 3,968,530 | 7/1976 | Dyson | 5/338 |
| 4,572,174 | 2/1986 | Eilender et al. | 128/149 |
| 4,959,059 | 9/1990 | Eilender et al. | 604/358 |
| 5,012,801 | 5/1991 | Feret | 128/155 |
| 5,188,124 | 2/1993 | Feret | 128/889 |
| 5,462,519 | 10/1995 | Carver | 602/47 |

*Primary Examiner*—Michael A. Brown
*Attorney, Agent, or Firm*—Chernoff, Vilhauer, McClung & Stenzel, LLP

[57] ABSTRACT

A skin-protective device and a method for protecting skin against abrasion by attaching a pair of mutually overlying membranous layers to an area of a person's skin with only the peripheries of the layers interconnected with each other, so that the layers can slip along each other. An absorbent pad may be placed between one of the layers and the skin, and a quantity of a lubricant can be contained between the layers. The device is thin, to avoid causing pressure when it is used in restricted spaces, as within one's shoe.

17 Claims, 2 Drawing Sheets

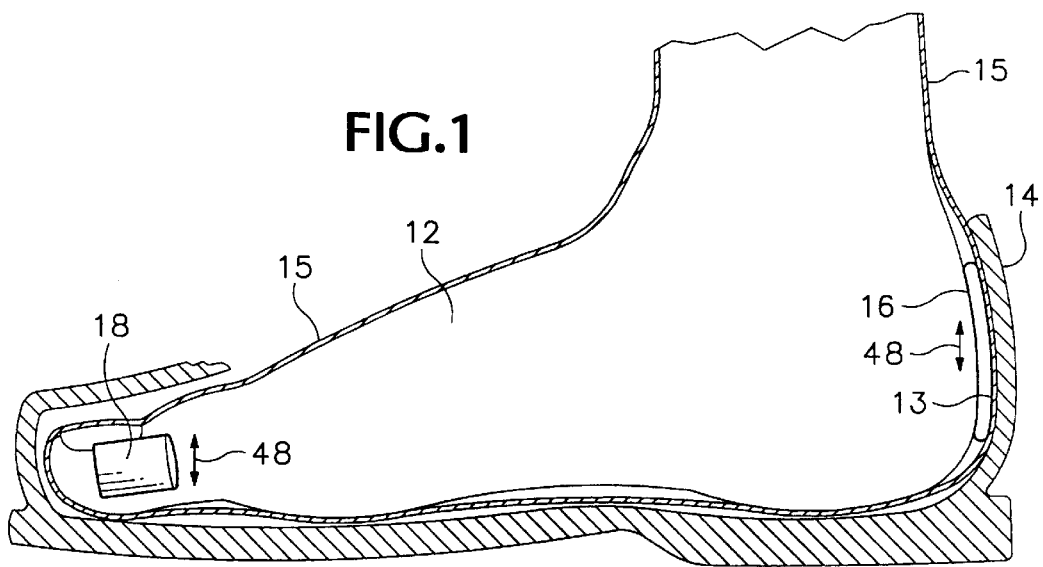
FIG. 1
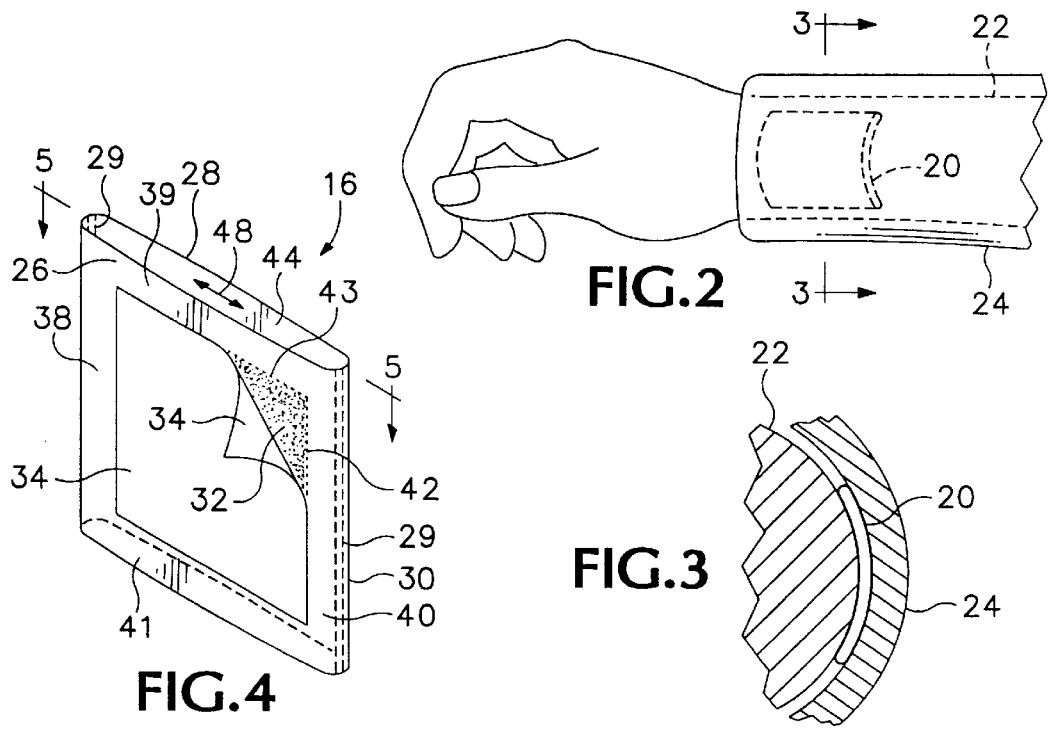
FIG. 2
FIG. 3
FIG. 4
FIG. 5

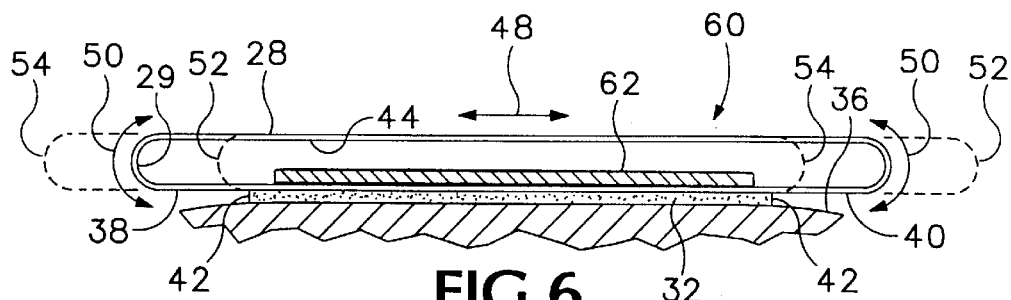
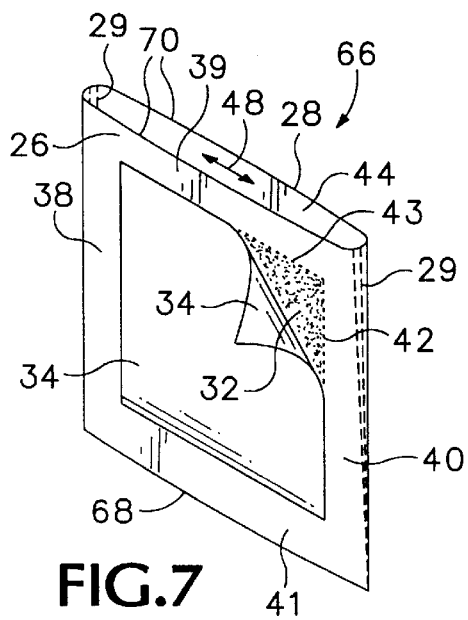
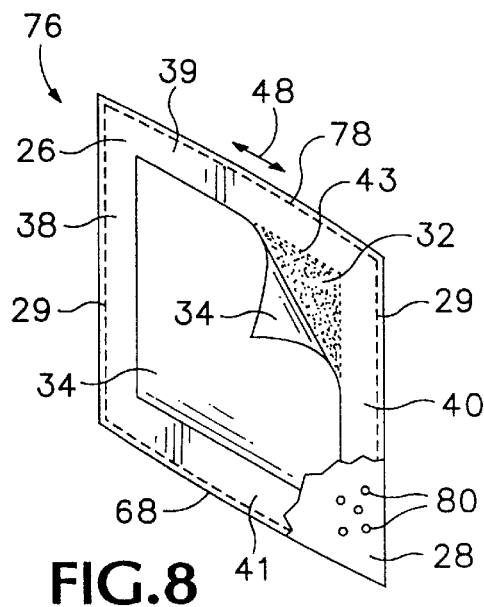
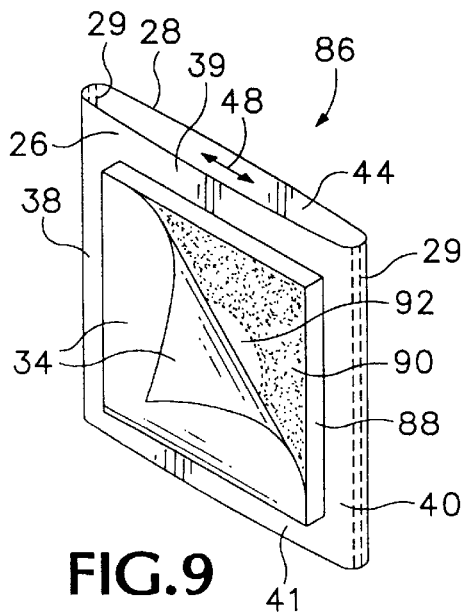
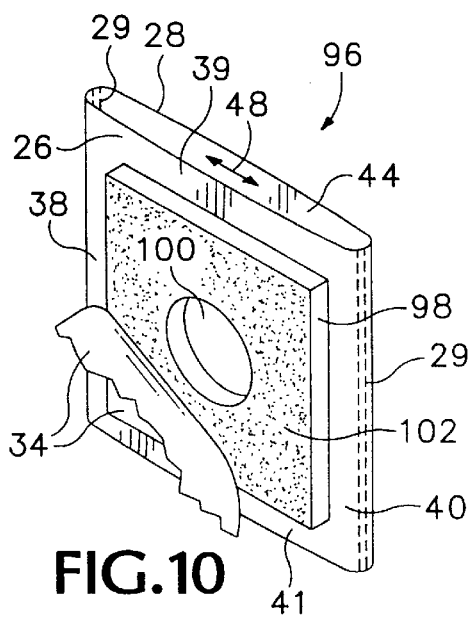

PROTECTING SKIN FROM FRICTION

BACKGROUND OF THE INVENTION

The present invention relates to avoidance and treatment of irritation resulting from friction or pressure against an area of skin.

It is well known that poorly fitting shoes, gloves, and other clothing can rub a person's skin and thereby cause significant irritation, soreness, or blisters, or may rub away a portion of the skin's surface. Such irritation by friction can be caused by straps of undergarments, by the rubbing of casts on the skin thinly covering a joint, such as a person's wrist within such a cast, or by athletic clothing or equipment rubbing a person's skin, as when a person is riding a bicycle or performing other physically demanding exercise over an extended time, particularly when there is pressure against the skin. Soreness may also be caused by friction against the skin of person in a wheelchair or confined to bed for a long time.

Attempts to avoid injury of skin by such friction in the past have included the use of devices intended to slip easily along the surface of the skin, as disclosed in Eilender et al. U.S. Pat. Nos. 4,959,059 and 4,572,174. Approaching the problem in another way, dressings intended to slip easily over adjacent materials are disclosed in Feret U.S. Pat. Nos. 5,012,801 and 5,188,124.

Various other devices have been intended to protect an irritated area of a person's skin by providing a structure supported by adjacent skin to push irritant surfaces away from irritated skin, or to equalize pressure on areas of a person's skin likely to be irritated. Such devices are disclosed in Kaufman U.S. Pat. No. 1,913,928, Scholl U.S. Pat. No. 2,098,312, Spence U.S. Pat. No. 3,548,420, Grubel U.S. Pat. No. 3,821,954, Gallovich U.S. Pat. No. 3,260,261, and Dyson U.S. Pat. No. 3,968,530. An inflatable pad for protecting bedsores is disclosed by Carver U.S. Pat. No. 5,462,519.

The devices disclosed in the patents mentioned above however, have not proved entirely satisfactory, for various reasons. Many of the devices previously known have acted as pads, but have not satisfactorily protected skin against the effects of friction and pressure against an adjacent surface. Such friction causes the skin to be pulled in directions parallel to its surface, generating shear forces within the skin that eventually irritate and cause injury to the skin, despite the use of the previously known devices for protecting the skin. Additionally, the previously known devices, with few exceptions, have had a thickness which of itself increases the pressure of an adjacent surface against skin in many situations, such as where a shoe fits poorly.

Consequently, what is still needed is an improved device for protecting a person's skin from the causes of friction. Preferably such an improved device should be thin, to avoid adding to pressure on the skin, should greatly reduce friction between the skin and an adjacent surface, should be easily and cheaply manufactured, and should be easy to use.

SUMMARY OF THE INVENTION

The present invention overcomes the shortcomings of the prior art devices mentioned above and provides an improved device for protecting a person's skin from injury or irritation, as well as a method of protecting one's skin by use of such a device. The skin-protective device of the present invention is thin and includes a pair of overlying layers of thin flexible membranous material attached to one another only at peripheral locations, leaving the two layers free to slip relative to each other with very little opposing friction, in response to relative movement between a person's skin and an adjacent surface of clothing, a cast or the like. The device is attached to the skin or the adjacent surface by an adhesive.

In a preferred embodiment of the invention the overlying flexible layers are provided in the form of an open-ended length of a flattened thin-walled tube of synthetic plastic material. In that embodiment of the invention the overlying layers of membranous material are interconnected along a pair of parallel opposite margins of each. A layer of an adhesive material attached to an outer surface of one of the layers has an area smaller than the area of each layer, so that marginal portions of the layers extend beyond the margins of the layer of adhesive material in at least two opposite directions.

In another embodiment of the invention the overlying layers are interconnected along the entire periphery of each layer, and a small amount of a lubricating material is located between the layers.

In one embodiment of the invention the overlying layers are of a thin breathably porous membranous material.

In a further embodiment of the invention, a thin pad of absorbent material is located between the layer of adhesive material and the outer surface of one of the overlying membrane layers and may be used to carry medication to the surface of the skin, or to absorb fluids from the skin.

In yet a further embodiment of the invention a thin pad of cushioning material may define an opening to receive a raised portion of the skin, such as a blister.

According to the method of the invention, skin is protected against irritation by attaching a device such as one of those just described to a person's skin, or to an adjacent surface, or between two adjacent layers of clothing or equipment that move relative to each other and one of which bears on the skin, and thereby significantly reducing friction resulting from such movement, so that the relative movement does not cause an irritating amount of stress on the skin adjacent the device.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a side elevational view of a person's foot in a partially cut-away sock and shoe, showing a pair of protective devices according to the present invention in use.

FIG. 2 is a view of a person's hand and a portion of an arm covered by a cast.

FIG. 3 is a sectional view taken along line 3—3 of FIG. 2, showing a device according to the present invention in use to protect the skin of the person's arm.

FIG. 4 is a perspective view of one of the skin-protective devices shown in FIG. 1.

FIG. 5 is a section view, taken along line 5—5, of the skin-protective device shown in FIG. 4, showing the device attached to a person's skin.

FIG. 6 is a view similar to that of FIG. 5 showing a skin-protective device which is an alternative embodiment of the present invention.

FIG. 7 is a perspective view of a skin-protective device which is another alternative embodiment of the present invention.

FIG. 8 is a partially cut-away perspective view of a skin-protective device which is yet a further alternative embodiment of the present invention.

FIG. 9 is a perspective view of a skin-protective device embodying the present invention and including a padding member.

FIG. 10 is a perspective view of a skin-protective device embodying the present invention and including a padding member defining an opening to surround an area of a person's skin.

DETAILED DESCRIPTION OF THE PREFERRED EMBODIMENTS

Referring now to the drawings which form a part of the disclosure herein, in FIG. 1 a person's foot 12 is inside a shoe 14, shown partly cut-away. A pair of devices according to the present invention, a larger skin-protective device 16 and a smaller skin-protective device 18, are both adhesively attached to the foot 12 to protect its skin against being irritated by movement of the foot 12 relative to the inner surface 13 of the shoe 14. A sock 15 is worn on the foot 12, between it and the inner surface 13 of the shoe 14, and the skin-protective devices of the present invention are shown being used between the foot 12 and the sock 15 within the shoe 14. Alternatively, the protective devices could be located between the sock 15 and the inner surface 13.

As shown in FIG. 1, the protective devices 16 and 18 are attached adhesively directly to the skin of the foot 12, but the same devices might also be adhered to the inside surface 13 of the shoe 14 or to either the inside or the outside of the sock 15. In each case, the skin-protective devices 16 and 18 serve to reduce the frictionally transmitted forces acting on the skin of the foot 12 as a result of movement of the inside surfaces 13 of the shoe 14 relative to the skin of the foot 12.

As shown in FIGS. 2 and 3, a skin-protective device 20 similar to the device 16 is attached adhesively to the skin of a person's arm 22 where the arm 22 is covered by a cast 24, to protect the skin from irritation as a result of relative movement between the skin and the inside of the cast 24. This can be of particular value in locations such as where bones, as at the wrist, are covered by only a thin layer of tissue including the skin. A similar situation could be found in the case of other orthopedic devices, such as in the attachment of a prosthetic limb, or where orthopedic braces bear against the skin of a natural limb.

The skin-protective devices 16, 18, and 20 are all of similar construction, except that their sizes are different, chosen to be applicable to each particular situation, so that the skin-protective device 16 utilized on the heel of the foot 12 is larger than the skin-protective device 18 used to protect the skin of a toe of the foot 12. As shown in FIG. 4, the protective device 16 comprises a pair of overlying parallel layers 26, 28 of a thin flexible membranous material attached to each other along respective peripheral margins, in a narrow area of connection indicated in broken line at 29, but otherwise not connected to each other. The layers 26 and 28 thus may be opposite sides of a flattened tube 30 of flexible, thin, synthetic plastic film For example, the tube 30 may be of polyethylene, with a wall thickness of about 0.001 inch. The thickness used should be great enough to have strength to avoid being torn in use, but otherwise as thin as practical, to be able to conform easily and not to add to pressure on the skin by the thickness of the device 16. Alternatively, the layers 26 and 28 may be of a slippery yet porous material such as an expanded PTFE in order to allow moisture to evaporate from the skin through the device 16, enhancing comfort and enabling the skin to resist pressure and friction by helping to keep the skin dry.

Attached to a central area of the outer surface of the layer 26, that is, on the side of layer 26 facing away from the layer 28 and thus on the outside of the tube 30, is a layer 32 of an adhesive material. The adhesive material is preferably a flexible, pressure-sensitive adhesive, covered until the device is to be used by a protective sheet 34 of a material such as a plastic-coated paper that can easily be peeled away from the layer 32 of adhesive material. The adhesive material of the layer 32 can be used to attach the protective device 16 to a person's skin or to an article of clothing such as the inside surface 13 of a shoe, or to a sock 15, at a location where the shoe or clothing is likely to be in contact with and to move relative to the adjacent skin. One suitable adhesive material is a hypoallergenic pressure sensitive acrylate adhesive, such as one available from 3M Medical Specialties Department, of St. Paul, Minn., in the form of product No. 1512, a transparent polyethylene film coated on both sides with the adhesive, and provided with a paper liner to serve as the protective sheet 34 in use.

As may be seen in FIG. 5, when the protective device 16 is attached to a person's skin 36 by the adhesive material 32, portions 38 and 40 of the layer 26 extend beyond the side margins 42 of the layer 32 of adhesive, which is located in and defines a central area of the layer 26. Similarly, portions 39 and 41 extend beyond the top margin 43 and a bottom margin of the layer 32 of adhesive material, although such extension of the top and bottom margins is of somewhat lesser importance.

The opposite inner surfaces 44 of the overlying layers 26 and 28, that is, the inner surfaces of the flattened tube 30, have a very small coefficient of friction relative to each other, preferably as a result of the material of which the overlying layers 26 and 28 are made. Thus, when a surface such as the inside surface 13 of the shoe 14 moves relative to the foot 12, particularly in either of the directions shown by the arrows 48 in FIGS. 1 and 5, the inside surfaces 44 slide along each other. The protective device 16 thus transmits only a very small amount of force between the inside surface 13 and the skin 36 by friction, so long as the extent of movement is limited. As the inside surfaces 44 slide along each other, one of the extending parts 38 and 40 of the layer 26 rolls from its original position into the position formerly occupied by a portion of the layer 28, as indicated by the arrows 50 in FIG. 5. Similarly, a portion of the layer 28 moves into a new position as an additional extension of the original location of the layer 26. As the layer 28 moves toward the right as shown in FIG. 5 the portions 38 and 40 of the flattened tube 30, extending beyond the central area where the adhesive layer 32 is located and including the connection portions 29 interconnecting the layers 26 and 28, assume the positions indicated by reference numerals 52. When the layer 28 moves leftward relative to the layer 26, the portions 38 and 40 and the connections 29 of the flattened tube 30 move toward the positions indicated by the reference numeral 54. Further movement of the layer 28 relative to the layer 26 is limited by the adhesive attachment of the device 16 to the skin 36 (or to a sock or a surface such as the inside surface 13, depending on where the device 16 is placed).

While the device 16 is shown in FIGS. 4 and 5 as having a significant distance between the opposing inside surfaces 44, the distance is actually greatly exaggerated in the drawings, to illustrate more clearly the rolling movement of the portions 38 and 40 as the inner surfaces 44 of the layers 26 and 28 slide along each other. In actual use of the device 16 the opposing inside surfaces 44 normally are directly in contact with each other. The tube-like structure of the device 16 provides the layers 26 and 28 freedom to move relative to each other farthest in the direction indicated by the arrows 48.

As mentioned above, ample flexibility of the material of which the layers 26 and 28 are made is desired. Such flexibility of the parts 38 and 40 extending beyond the margins 42 of the central area including adhesive material 32 permits movement of the layers 26 and 28 relative to each other in other directions, as well as the directions of the arrows 48. Thus the device 16 reduces the amount of friction where there is relative movement in any direction between an area of skin 36 being protected by the device 16 and an adjacent surface, such as the inside surface 13 of the shoe 14. However, since the freedom of movement of the layers 26 and 28 relative to each other is greatest in the direction indicated by the arrows 48, it is preferred to apply the device 16 to the skin 36 oriented in the way in which the greatest amount of expected relative movement of an adjacent surface against the skin 36 is parallel with the arrow 48.

Referring now to FIG. 6, in a slightly different embodiment of the invention a protective device 60 is generally similar to the protective device 16, and like reference numerals are used for like parts. The device 60 differs, however, in that between the inside surfaces 44 of the layers 26 and 28 there is provided a layer of a soft slippery material such as a piece 62 of a thin satin cloth. Such a slippery material is attached to an inside surface 44 of the layer 26, in an area preferably coextensive with or smaller than the area of the layer 32 of adhesive material, where it enhances the ability of the layers 26 and 28 to move relative to each other between the surface of the skin 36 and an adjacent surface such as the inside surface 13 of the shoe 14.

While the protective devices 16 and 60 have been illustrated as having the form of a flattened tube 30, it will be understood that it is also possible to manufacture such devices in more than one way, including placement of separately fashioned layers 26 and 28 of suitable material into appropriate positions overlying one another, and thereafter interconnecting respective marginal portions of those layers, to form the linear connections 29 between the layers 26 and 28 (FIG. 4). These connections 29 are preferably as smooth and flexible as practical, and are free to move as indicated by the arrows 50 (FIGS. 5, 6) as the layers 26 and 28 move relative to each other.

Depending upon the location on a person's skin where a protective device according to the invention is intended to be used, it may also be desirable to interconnect the layers 26 and 28 with each other as in the skin-protective device 66 shown in FIG. 7. There, the layers 26 and 28 are also held together by a narrow connection along a margin 68, so that the layers 26 and 28 are interconnected with each other along three sides of the rectangular skin-protective device 66 shown in FIG. 7. The layers 26 and 28 remain unconnected along the remaining margin 70, and are free to slide easily relative to each other with some flexure occurring along the margin 68.

A protective device 76, shown in FIG. 8, is generally similar to the device 66 shown in FIG. 7, except that both the bottom margin 68 and a top margin 78 of the device are closed by a linear connection so that the peripheral connections of the layer 26 to the layer 28 completely circumscribe, but are spaced outwardly apart from the central area including the layer 32 of adhesive material, forming a closed envelope of the two overlying layers 26 and 28. The resulting envelope may contain a very small amount of a lubricant, such as a few droplets 80 of a suitable oil or a small amount of a lubricant powder. The quantity of such a lubricant is intentionally kept small, so that it serves merely as a lubricant to permit the layers 26 and 28 to move relative to each other between a person's skin 36 and an opposing surface, without causing the protective device 76 to have a significant thickness that could increase the pressure of an adjacent surface of a shoe or other article against the skin intended to be protected by the device 76.

A protective device 86, shown in FIG. 9, includes structure generally similar to the protective device 16 shown in FIG. 4. Additionally, there is a thin pad 88 adhered to the outer surface of the layer 26, and a layer 90 of adhesive material overlies the thin pad 88. The adhesive material of the layer 90 is preferably limited to marginal portions of the thin pad 88, leaving a center part 92 of the pad 88 free from adhesive material. This center part 92 is thus available to absorb exudate from a blister or an area of previously irritated skin over which the skin-protective device 86 may be applied. Additionally, the thin pad 88 may be impregnated with medication prior to placement of the protective device 86 on a person's skin. The medication is thus held in contact with the underlying skin to promote healing while the protective device 86 reduces friction and thus protects the skin from further irritation and injury that might otherwise be caused by the rubbing of an adjacent surface of an article of clothing or the like.

A skin-protective device 96 shown in FIG. 10 is generally similar to the protective device 86 shown in FIG. 9, but in place of the thin pad 88 of the device 86 there is a thin pad 98 that defines an opening 100, surrounded by a layer 102 of an adhesive material. The thin pad 98 can thus be adhesively attached to a person's skin, surrounding a raised or swollen injured area such as a blister, providing some additional spacing between the irritated surface of the skin and an adjacent surface. At the same time, the protective device 96 reduces friction and allows the adjacent surface to move easily relative to the skin when it is attached to the skin.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A skin-protective device, comprising:
   (a) a pair of overlying parallel protective layers of membranous material overlying one another, each of said layers extending outwardly beyond a central area thereof;
   (b) said layers being joined to each other in a connection located outwardly apart from said central area;
   (c) each of said layers having an inner face and an outer face, said inner faces confronting each other and being free to slide along each other over at least a limited distance; and
   (d) a layer of a flexible adhesive material located wholly within said central area, on an outerface of one of said layers.

2. The skin-protective device of claim 1, said connection including a narrow strip extending along a peripheral line spaced outwardly apart from said central area.

3. The skin-protective device of claim 1, said layers of membranous material including respective portions of a collapsed tube having a thin flexible wall structure and a pair of open ends, each of said layers including a portion of one of a pair of opposite sides of said tube.

4. The skin-protective device of claim 1 wherein each of said layers of membranous material is a thin film of a synthetic plastic material.

5. The skin-protective device of claim 1 wherein said connection completely circumscribes said central area, and wherein a quantity of a lubricant is enclosed between said layers within an area defined by said connection.

6. The skin-protective device of claim 1 including an absorbent layer attached to one of said layers of membranous material, between said outer face thereof and said layer of adhesive material.

7. The skin-protective device of claim 6 wherein said absorbent layer is medicated.

8. The skin-protective device of claim 6 wherein said absorbent layer defines an opening therethrough that is large enough to surround a blister.

9. The skin-protective device of claim 1 including a removable adhesive-protecting sheet attached to and covering said layer of adhesive material.

10. The skin-protective device of claim 1 wherein at least one of said layers of membranous material is of breathably porous material.

11. The skin-protective device of claim 1 wherein said layers of membranous material are separate and free to move relative to each other along at least a part of a periphery thereof.

12. A method of protecting skin against irritation, comprising the steps of:

(a) placing a device including a pair of layers of thin flexible membranous material between an area of skin intended to be protected and an adjacent surface confronting said area of skin;

(b) attaching one of said layers to a selected one of said skin and said adjacent surface by the use of an adhesive, said pair of layers thereby separating said area of skin from said adjacent surface; and (c) in response to movement of said adjacent surface relative to said area of skin, moving said layers of membranous material along one another over a limited range of movement, with a coefficient of friction between said layers that is substantially smaller than a coefficient of friction that would otherwise be present between said skin and said adjacent surface absent said pair of layers.

13. The method of claim 12 including the further step of providing an absorbent layer attached to one of said layers of membranous material and located between said layers of membranous material and said area of skin.

14. The method of claim 13 wherein said absorbent layer defines an opening therethrough and including the step of placing said device against said area of skin in a position thereon in which said opening is aligned with a previously irritated portion of said area of skin.

15. The method of claim 12 wherein said adjacent surface is an interior surface of a garment.

16. The method of claim 12 wherein said adjacent surface is an interior surface of a cast.

17. The method of claim 12 wherein said adjacent surface is an interior surface of an orthopedic support device.

* * * * *